(12) United States Patent
Bruno et al.

(10) Patent No.: US 9,687,849 B2
(45) Date of Patent: Jun. 27, 2017

(54) LEAK PROOF, AIR TIGHT PLASTIC CONTAINER DEVICE

(71) Applicant: IGU Holdings, LLC, Cheyenne, WY (US)

(72) Inventors: Albert R. Bruno, McKees Rocks, PA (US); Alex V. Strahan, McKees Rocks, PA (US)

( * ) Notice: Subject to any disclaimer, the term of this patent is extended or adjusted under 35 U.S.C. 154(b) by 0 days.

(21) Appl. No.: 14/732,709

(22) Filed: Jun. 6, 2015

(65) Prior Publication Data

US 2016/0354775 A1  Dec. 8, 2016

(51) Int. Cl.
| | | |
|---|---|---|
| *B65D 41/00* | (2006.01) | |
| *B01L 3/00* | (2006.01) | |
| *B65D 1/16* | (2006.01) | |
| *B65D 43/02* | (2006.01) | |
| *G01N 1/10* | (2006.01) | |

(52) U.S. Cl.
CPC ........... *B01L 3/508* (2013.01); *B01L 3/50825* (2013.01); *B65D 1/16* (2013.01); *B65D 43/02* (2013.01); *G01N 1/10* (2013.01); *B01L 2200/0689* (2013.01); *B01L 2200/185* (2013.01); *B01L 2300/042* (2013.01); *B01L 2300/12* (2013.01)

(58) Field of Classification Search
CPC ...... B65D 2543/00555; B65D 43/0218; B65D 41/0414; B65D 41/185
USPC ........................ 215/354, 355; 220/FOR. 203
See application file for complete search history.

(56) References Cited

U.S. PATENT DOCUMENTS

| | | | | |
|---|---|---|---|---|
| 5,207,341 A | * | 5/1993 | Yeager | B65D 1/0246 215/246 |
| 5,954,215 A | * | 9/1999 | Alter | B65D 41/17 215/318 |
| 7,854,344 B2 | * | 12/2010 | Suk | B65D 43/0212 220/318 |
| 8,608,009 B2 | * | 12/2013 | Ogawa | B65D 43/0231 215/252 |
| 2005/0150890 A1 | * | 7/2005 | Wang | B65D 43/0212 220/256.1 |
| 2007/0175853 A1 | * | 8/2007 | Kebben | B65D 41/185 215/344 |
| 2009/0236354 A1 | * | 9/2009 | Alvares | B65D 43/021 220/783 |
| 2014/0158688 A1 | * | 6/2014 | Loughrin | B65D 41/185 220/304 |

* cited by examiner

*Primary Examiner* — Shawn M Braden
(74) *Attorney, Agent, or Firm* — Gwen R. Acker Wood; Acker Wood IP Law, LLC

(57) ABSTRACT

The present invention provides an improved, leak proof, air tight, cost-effective, plastic liquid specimen container device and methods of use, comprised of a container, a lid, a lid groove containing a gasket therein that is configured to cover and tighten over the rim of the container, a lid flange, and a thin hook in the container containing a second gasket that is compressed by the lid flange when the lid is closed over the container. The improved container device of the present invention thus provides two, independent, internal seals that protect the liquid contents therein for extended periods of time, even if the plastic undergoes deformation, during transport, especially air transport, and under varying temperature and atmospheric pressure.

5 Claims, 9 Drawing Sheets

LEAK PROOF, AIR TIGHT PLASTIC CONTAINER DEVICE

FIELD OF THE INVENTION

The present invention relates to medical laboratory equipment and, in particular, to an improved, leak proof, air tight, cost-effective liquid specimen plastic container.

BACKGROUND OF THE INVENTION

Body fluids, such as urine, routinely are taken from individuals by medical personnel for laboratory analysis. The typical specimen is collected at one location, such as a medical doctor's office or hospital, and then transported to a clinical laboratory site where the specimen is subjected to analysis. The specimen usually is collected in a plastic container that is shipped in the same container. The laboratory site may be quite distant from the collection site and the specimen container often is forwarded by mail, including air mail. To maintain the integrity of the sample it is necessary that the specimen container be leak proof and air tight to prevent fluid loss and possible air contamination during handling while in transport, especially when subjected to reduced atmospheric pressure that may occur during air transport.

Conventional plastic specimen containers with removable lids for medical purposes are not completely leak proof and air tight. Plastic specimen containers which purport to be leak proof and/or air tight usually include intricate sealant design features which can be costly to manufacture, or require sealant materials placed over external areas of the container where the container and its lid engage, without which complete fluid retention and air-tightness in the container cannot be ensured. Complete sealant properties are especially necessary when the plastic container is stored for an extended period of time, where it is likely that the plastic container will undergo slight deformations in shape due to temperature and pressure changes, resulting in fluid leakage as well as slow air seepage into and out of the container.

A need exists, therefore, for an improved plastic container for collection and transport of medical specimens which is completely leak proof and air tight for extended periods of time and under varying temperatures and atmospheric pressure without the need for costly manufacturing sealant design features or additional external sealant materials.

SUMMARY

The present invention fulfills this need by providing an improved, cost-effective, plastic medical specimen container device that is completely leak proof and air tight for extended periods of time and environmental conditions, such as mechanical stressors and varying temperature and atmospheric pressure.

In particular, the present invention provides a leak proof, air tight, plastic specimen container device comprising a container and a lid. The container is comprised of a circumferential sidewall having an inner surface and an outer surface, an upper rim of the side wall, and a bottom. Projecting into the interior of the container from the inner surface of the circumferential side wall located downwardly from the upper rim is a hook. The hook contains a gasket therein. A plurality of external screw threads projects downwardly from the upper rim on the outer surface of the circumferential side wall. The lid comprises an outer side and an inner side and a peripheral edge. A plurality of indentations project downwardly from the outer side of the peripheral edge, and a plurality of internal screw threads project downwardly from the peripheral edge of the inner side. Located on the inner side of the lid adjacent to the peripheral edge is an annular groove having a lid gasket therein. Adjacent to the annular groove is an annular flange on the inner side adjacent to the annular groove.

The lid of the container device is configured to rotatably screw on to the outside of the container by engagement of the internal screw threads of the lid with the external screw threads of the container. The lid flange is configured to insert into the hook when the lid is rotatably screwed on to the container. When the lid is closed on the container, the container gasket is compressed by the lid flange and the lid gasket is compressed by the upper rim of the container. The compression of the lid gasket and the container gasket completely seals the lid onto the container to prevent any leakage of the liquid sample from the interior of the container and any air seepage into or out of the interior of the container.

The volume capacity of the liquid contents of the container device may be, without limitation, 500 ml down to 40 ml, with all sizes in-between decreased from 500 ml in 20 ml increments.

The present invention also provides a method of collecting a liquid sample comprising placing the liquid sample in the leak proof, air tight, plastic specimen container device described above, and sealing the liquid sample in the container by engaging the internal screw threads of the lid with the external screw threads of the container, and rotating the lid in a screw-type fashion until resistance to the rotation is encountered. The method further comprises ensuring leak proof, air tight transport of the liquid sample during transport from the site of specimen collection to a different site for laboratory analysis.

BRIEF DESCRIPTION OF THE DRAWINGS

A fuller understanding of the invention can be gained from the following description when read in conjunction with the accompanying figures, where like reference numerals refer to identical or functionally similar elements throughout the separate views, which illustrate some, but not the only and exclusive, examples of embodiments of the invention and, as such, the figures disclosed herein are to be considered illustrative rather than limiting. In the drawings.

DETAILED DESCRIPTION OF THE INVENTION

Figure 1:
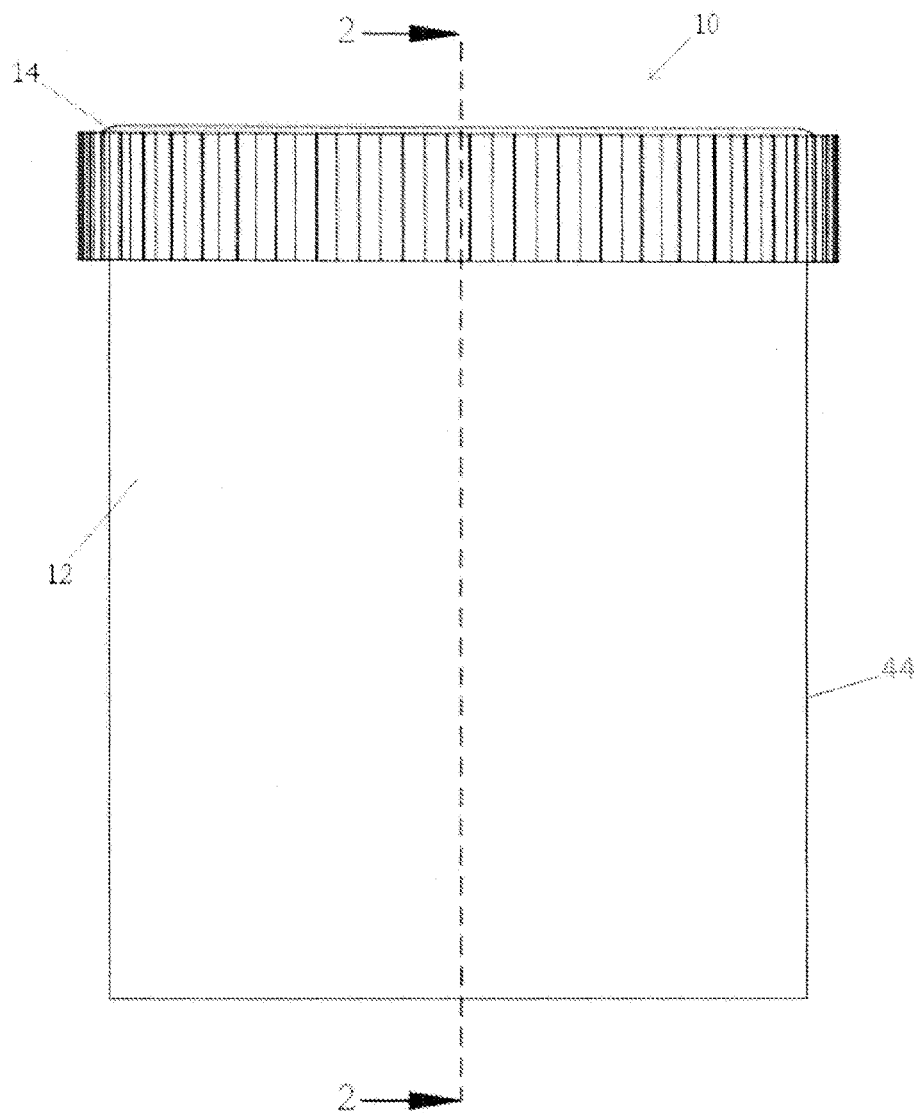
FIG. 1 is a front view of the plastic specimen container device shown with the lid in a closed position on the container in accordance with an embodiment of the invention.

Referring now to the drawings, the invention comprises an improved, leak proof, air tight, cost-effective, plastic container device 10 for collecting and transporting liquid specimens for laboratory analysis.

Figure 2:
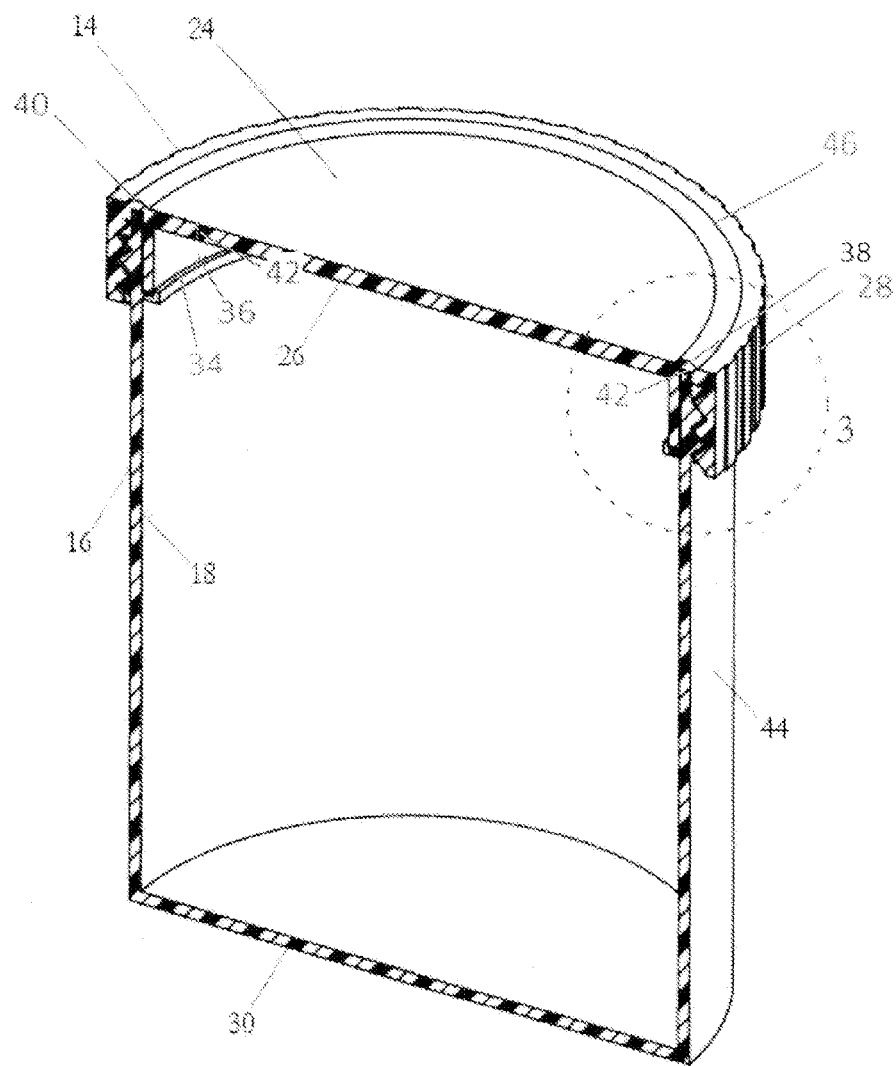
FIG. 2 is a perspective sectional view taken along line 2-2 of FIG. 1.
Figure 3:
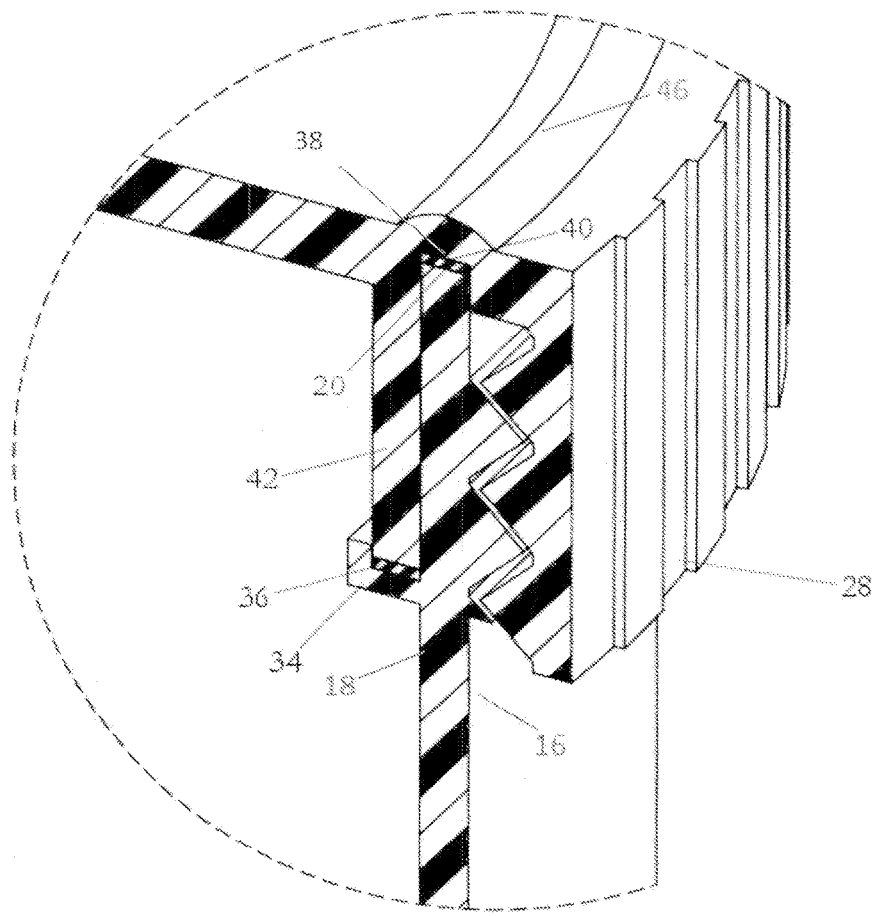
FIG. 3 is an enlarged view of section 3 encircled in FIG. 2.
Figure 4:
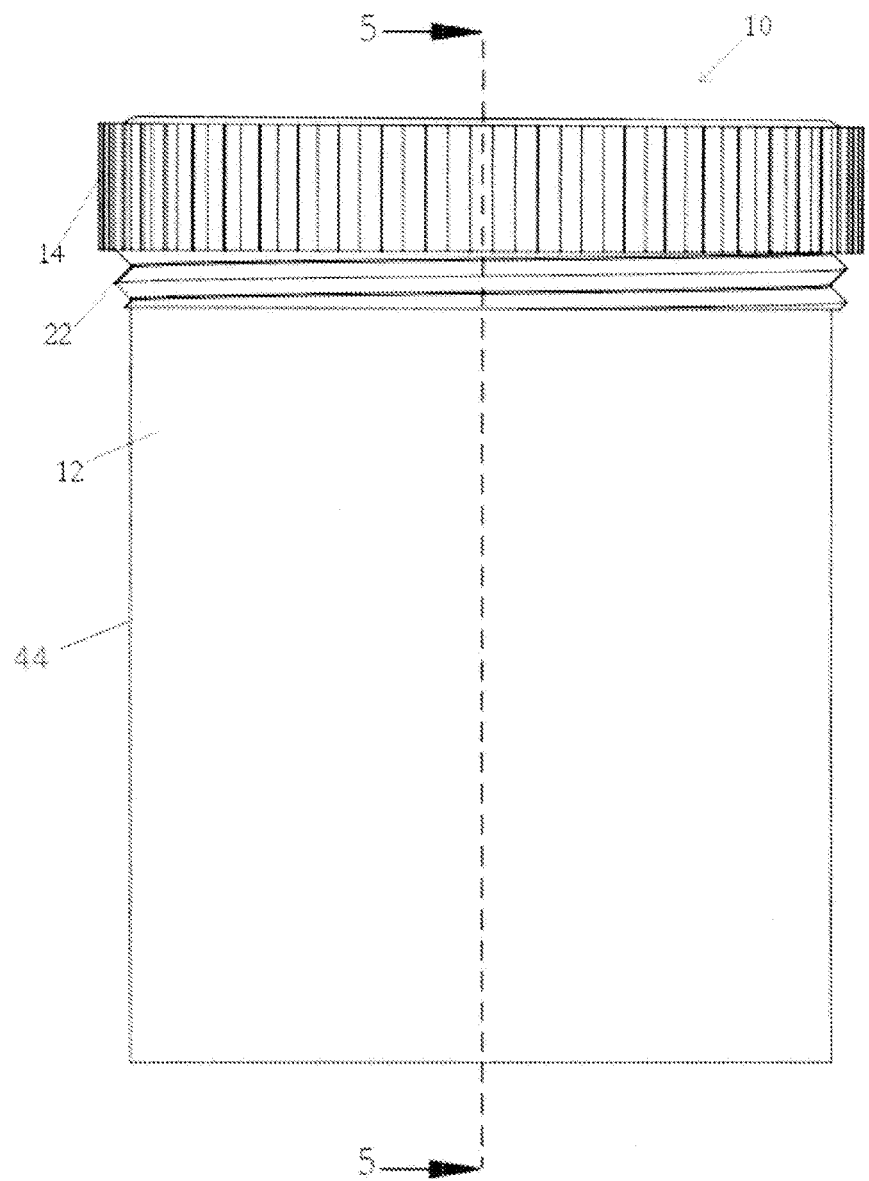
FIG. 4 is a front view of the plastic specimen container device shown with the lid in a partially opened position on the container in accordance with an embodiment of the invention.
Figure 5:
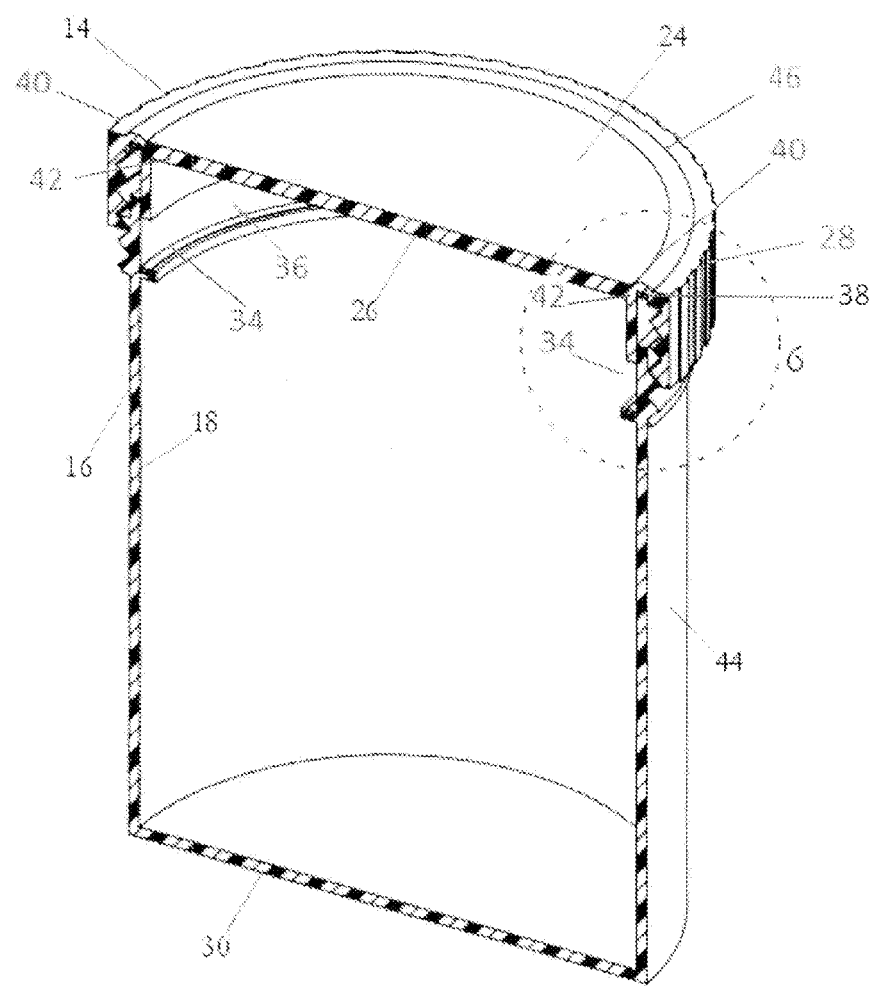
FIG. 5 is a perspective sectional view taken along line 5-5 of FIG. 4.
Figure 6:
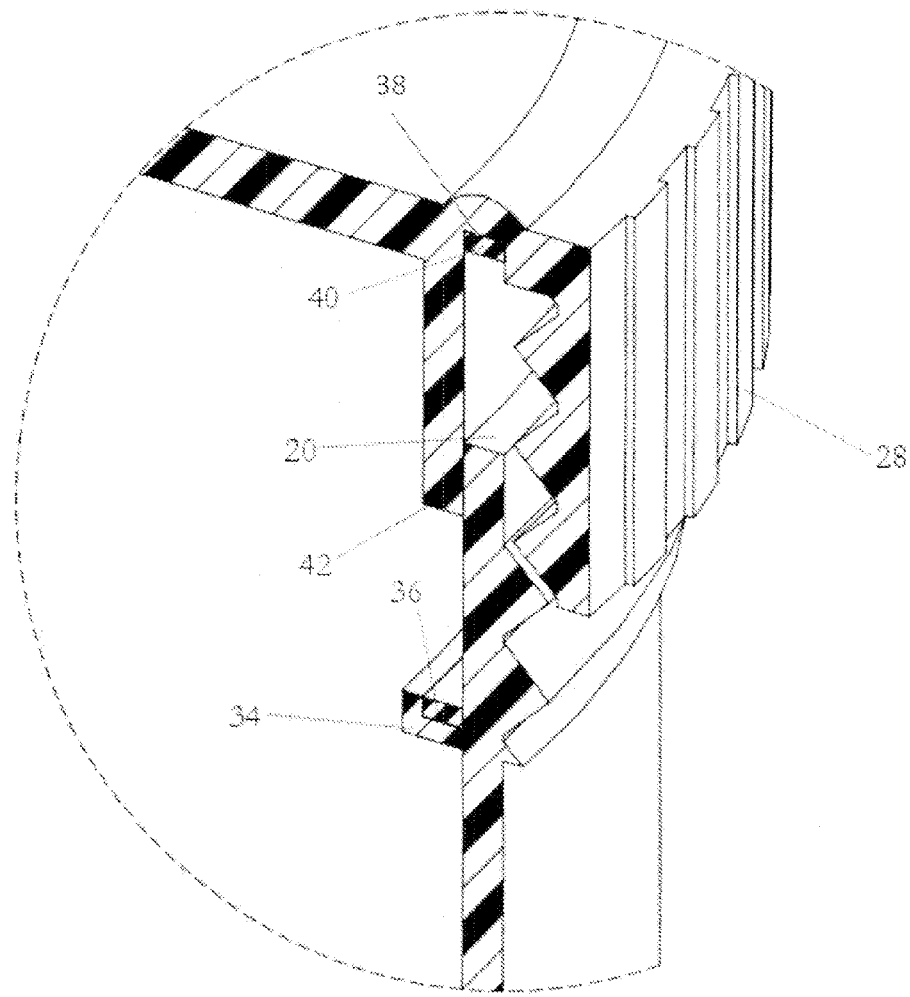
FIG. 6 is an enlarged view of section 6 encircled in FIG. 5.
Figure 7:
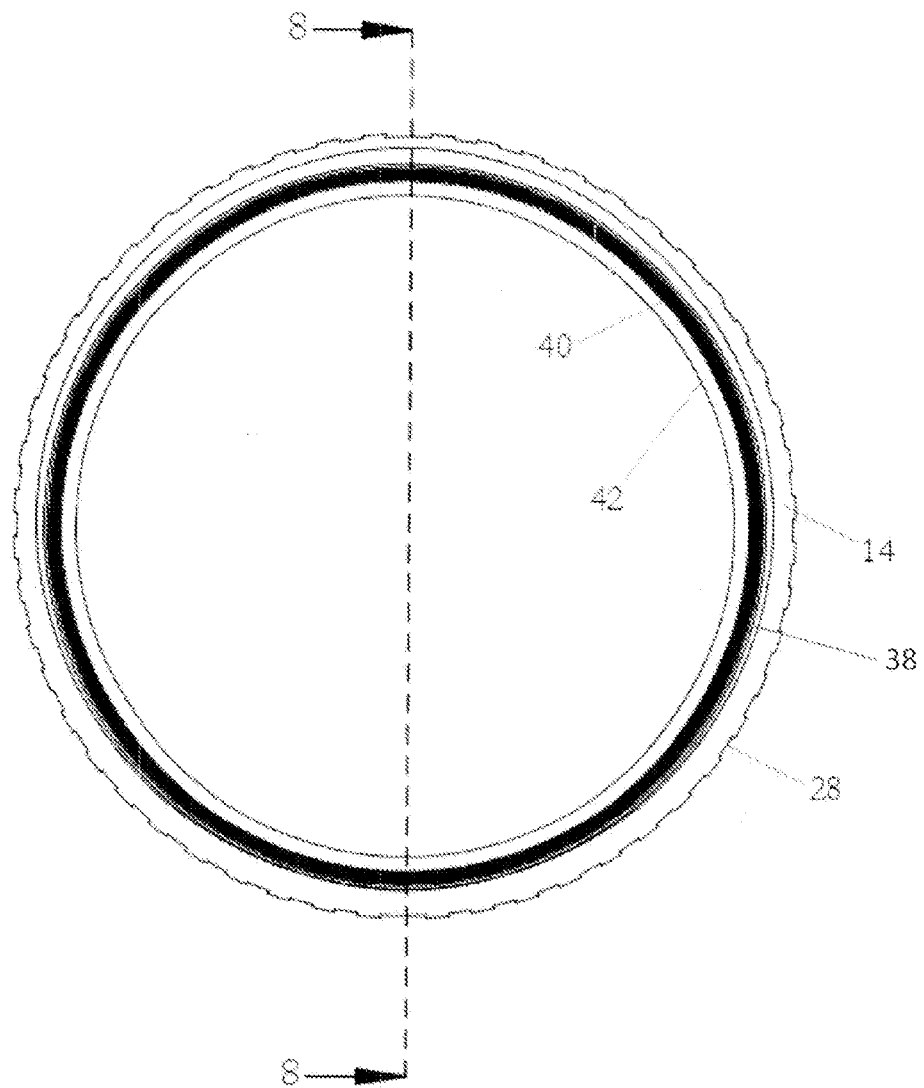
FIG. 7 is a top view of the inner surface of the lid of the plastic specimen container device in accordance with an embodiment of the invention.

As shown in FIGS. 1-6, the leak proof, air tight, plastic container device 10 includes a generally circular container 12 and a generally circular lid 14 that closes over and seals the container 12 (closed container shown in FIGS. 1-3; open container shown in FIGS. 4-6). The container 12 comprises an interior for holding a liquid sample, the interior bounded by a circumferential side wall 44, which has an outer surface 16, an inner surface 18, and a base 30. As best seen in FIGS. 3 and 5, the upper end of the side wall 44 terminates in an upper rim or edge 20 that is continuous with the outer surface 16 and the inner surface 18 of the container 12. Projecting downwardly from the upper rim 20 on the outer surface 16 of the container 12 are a plurality of annular external screw threads 22 oriented generally perpendicular to the side wall 44 of the container 12 (best seen in FIGS. 4 and 6). Continuous with the inner surface 18 of the upper rim 20 is a hook 34 located downwardly from the upper rim 20 for receiving a gasket therein (best seen in FIGS. 3 and 6). In an embodiment, the hook 34 is generally L-shaped hook.

Figure 8:
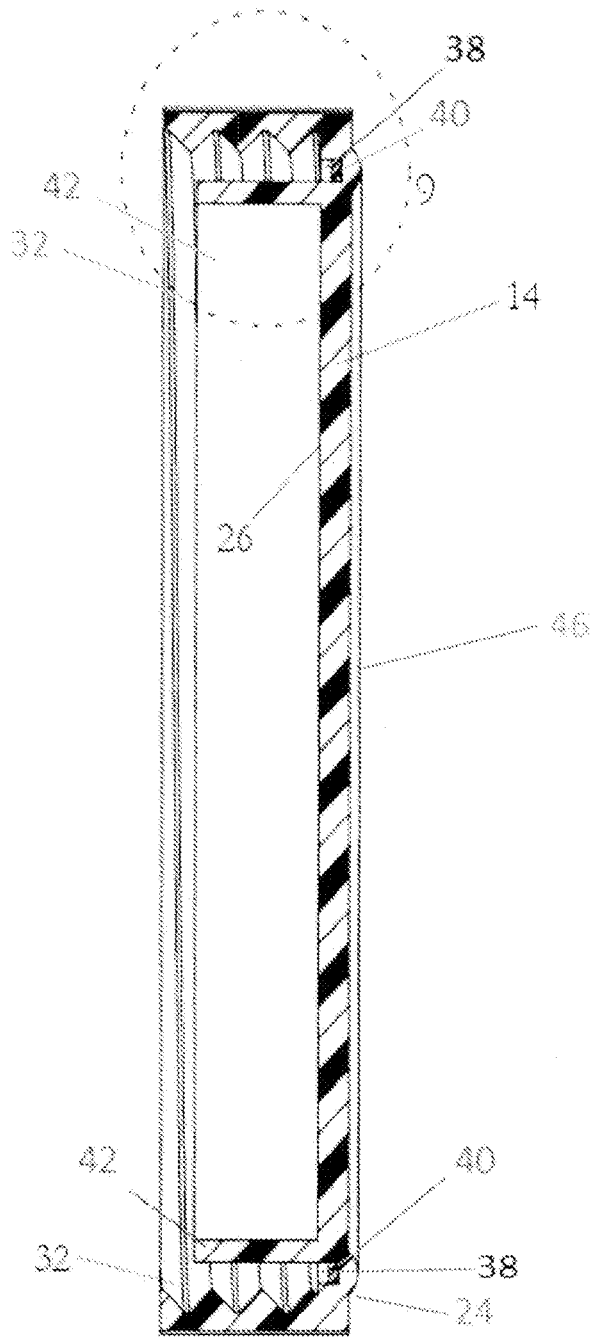
FIG. 8 is a sectional view taken along line 8-8 of FIG. 7.
Figure 9:
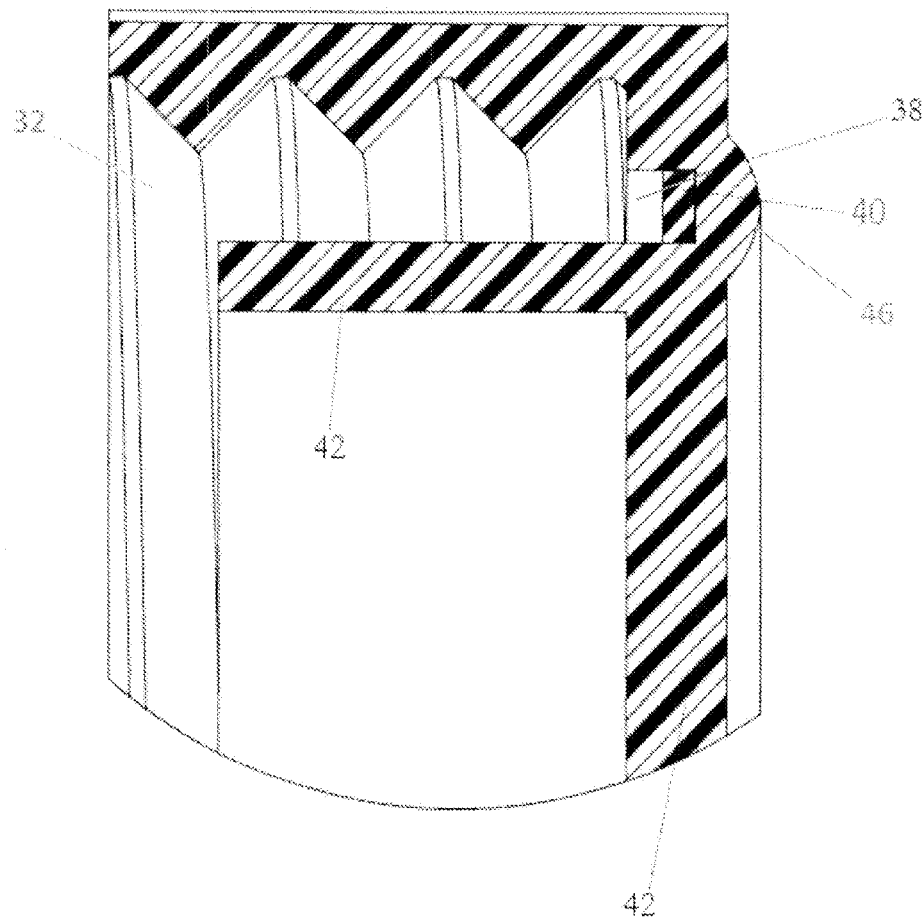
FIG. 9 is an enlarged view of section 9 encircled in FIG. 8.

As shown in FIGS. 2 and 5, the lid 14 includes an outer side 24 and an inner side 26. The periphery of the lid 14 projects downwardly from the outer side 24 of the lid 14 to form a shoulder which contains a plurality of indentations 28 oriented generally perpendicular to the outer side 24 of the lid 14. In use, the plurality of indentations 28 facilitates gripping the lid 14 when opening and closing the container 12. As shown in FIG. 8, adjacent to the periphery of the lid 14 on the inner side 26 is an annular groove 38 which protrudes slightly on the outer surface 24 of the lid 14 to form an annular bulge 46 (best seen in FIGS. 3, 6 and 9). As shown in FIG. 9, the groove 38 is a configured to receive a lid gasket 40 therein. Adjacent to the annular groove 38 is an annular flange 42. When the lid 14 is closed over the container 12, the lid gasket 40 in the annular groove 38 sits atop, completely covers, and is compressed upon the upper rim 20 of the container 12 to form a tight seal. The annular flange 42 inserts into the hook 34 in the container 12 which contains the container gasket 36 (best seen in FIGS. 3 and 6). Projecting downwardly from the periphery of the lid 14 on the inner side 26 are a plurality of annular internal screw threads 32 oriented generally perpendicular to the inner side 26 and the outer side 24 of the lid 14 (best seen in FIGS. 6, 8 and 9). The internal screw threads 32 of the lid 14 are configured to be complementary to and engage the external screw threads 22 of the container 12 so that the lid 14 rotatably closes on to the container 12 when moved in a direction parallel to the engaged screw threads. When resistance is encountered to rotation of the lid 14 on to the container 14, the container is effectively leak proof and air tight with the contents of the container 14 being completely sealed therein.

In an embodiment, the plastic container device 10 of the invention has a liquid capacity of 120 ml having the following dimensions: diameter of the lid 14 ranges from about 4.0 cm to about 8.0 cm; length of the lid screw threads 32 and the container screw threads 22 range from about 1.0 cm to about 2.0 cm; length of the container 12 from the bottom 30 of the container 12 to the bottom of the container screw threads 22 ranges from about 5.0 cm to about 8.0 cm; thickness of the container 12 from the inner side wall 16 to the outer side wall 18 ranges from about 0.5 mm to about 2.0 mm; length of the hook 34 from the upper rim 20 of the container 12 to the bottom of the hook ranges from about 1.0 cm to about 2.0 cm; outer width of the hook 34 ranges from about 2.0 mm to about 6.0 mm; diameter of the concave portion of the hook 34 ranges from about 1.0 mm to about 3.0 mm; length of the lid flange 42 ranges from about 0.5 cm to about 1.5 cm; width of the lid flange 42 ranges from about 1.0 mm to about 3.0 mm; and width of the container gasket 36 and the lid gasket 40 ranges from about 1.0 mm to about 3.0 mm.

In another embodiment, the plastic container device 10 has a liquid capacity of 120 ml with the following dimensions: diameter of the lid 14 is about 6.0 cm; length of the lid screw threads 32 and the container screw threads 22 is about 1.5 cm; length of the container 12 from the bottom 30 of the container 12 to the bottom of the container screw threads 22 is about 7.0 cm; thickness of the container 12 from the outer side wall 16 to the inner side wall 18 is about 1.3 mm; length of hook 34 from the upper rim 20 of the container 12 to the bottom of the hook is about 1.5 cm; outer width of the hook 34 is about 4.0 mm; diameter of the concave portion of the hook 34 is about 2.0 mm; length of the lid flange 42 is about 1.0 cm; width of the lid flange 42 is about 2.0 mm; and width of the container gasket 36 and the lid gasket 40 is about 2.0 mm.

In other embodiments of the invention, the volume capacity of the plastic container device 10 may be 500 ml, 480 ml, 460 ml, 440 ml, 420 ml, 400 ml, 380, 360 ml, 340 ml, 320 ml, 300 ml, 280 ml 260 ml, 240 ml, 220 ml, 200 ml, 180 ml, 160 ml, 140 ml, 100 ml, 80 ml, 60 ml or 40 ml, with dimensions for each volume capacity plastic container device increased or reduced proportionate to the dimensions disclosed above for the 120 ml plastic container device 10.

Suitable materials for manufacturing the container 12 and lid 14 include polymeric materials, which include, without limitation, polystyrene, polypropylene, polyethylene glycol, or any other suitable plastic material that has strength and durability.

Container and lid gaskets 36, 40 for use in the invention may be made from any suitable material, such as elastomers commonly used to manufacture gaskets, which includes, without limitation, rubber gaskets configured as O-rings. The shape of the gaskets 36, 40 may be, without limitation, rectangular, circular, D-shaped, or X-shaped. In an embodiment, the gaskets 36, 40 are rectangular. In an embodiment, the size of the two gaskets 36, 40 is identical. In another embodiment, the size of the two gaskets 36, 40 is different, with the container gasket 36 having a smaller size than the lid gasket 40. In all embodiments, the container gasket 36 and the lid gasket 40 used in the invention have a shape that provides for complete contact with their mating surfaces, i.e., the upper rim 20 and the lid flange 42, respectively.

During use, after a liquid sample is collected in the interior of the container 12, the lid 14 is closed over the container 12 by engagement of the complementary screw threads 22, 32 and rotatable movement of the lid 14. In use, when the lid 14 is being closed over the container 12, first the lid gasket 40 in the annular groove 38 mates with, and is compressed upon, the upper rim 20 of the container 12 to form a tight seal. Then, the annular flange 42 inserts into the hook 34 in the container 12 which contains the container gasket 36, which is compressed by the flange 42 to form a second tight seal. The lid flange 42 is configured to fit tightly in the hook 34 of the container 12 due to the lid flange 42 having a width that is substantially the same as the inner width of the hook 34. Further, the container gasket 36 used in the invention has a width that is substantially the same as the inner width of the container hook 34.

Importantly, therefore, when the lid 14 is closed over the container 12, the lid gasket 40 and the container gasket 36 form two independent, internal, tight seals so that the contents of the container is completely leak-proof and air tight. Further, in the event that the plastic container 12 and/or lid 14 is deformed in shape due to temperature or pressure changes in the environment, or because the plastic container 12 is stored for an extended period of time, because the gaskets 36, 40 are tightly compressed in their respective locations, the integrity of the leak proof and air tight seal is maintained, even from gradual air seepage into or out of the container 12, which typically occurs over time. The important advantage of the present invention, therefore, is the ability to completely seal the liquid contents of the container 12 from any leakage out, and from any air seepage into and/or out, of the container 12 for extended periods of time, due to the two internal, independent seals, and from environmental conditions, such as mechanical stressors, rigors encountered during transportation, especially air transport, and fluctuations in temperature and atmospheric pressure.

While the invention has been particularly shown and described with reference to embodiments described above, it will be understood by those skilled in the art that various alterations in form and detail may be made therein without departing from the spirit and scope of the invention, as defined by the appended claims.

What is claimed is:

1. A leak proof, air tight plastic specimen container device, comprising:
    a container comprising a circumferential side wall, said side wall having an inner surface and an outer surface and an upper rim, said inner surface defining an interior opening therein for holding a liquid sample, said side wall projecting downwardly from said upper rim, an L-shaped hook continuous with and protruding from the inner surface of the circumferential side wall and located downwardly from said upper rim, said hook having an upper surface containing a container gasket which fits atop the entire upper surface of the hook; a plurality of external screw threads projecting downwardly from the upper rim on the outer surface of the circumferential side wall, and a bottom; and
    a lid comprising an outer side and an inner side and a peripheral edge, a plurality of indentations projecting downwardly from the outer side of the peripheral edge, a plurality of internal screw threads on the peripheral edge of the inner side, an annular groove on the inner side of the lid adjacent to the peripheral edge having a lid gasket therein, and an annular, straight lid flange on the inner side adjacent to the annular groove, said lid configured to rotatably screw on to the outside of the container by engagement of the internal screw threads of the lid with the external screw threads of the container and to close the opening of the container by rotation of the lid in a screw-type fashion until resistance to the rotation is encountered, wherein the lid gasket in the annular groove is configured to mate with and be compressed atop the upper rim of the container to form a tight seal, wherein the annular straight lid flange is configured to insert into and atop the entire upper surface of the hook so that the container gasket therein is compressed under the annular straight lid flange to form a second, separate tight seal, wherein when the container gasket is compressed, the straight lid flange, the upper surface of the container hook and the container gasket all have substantially the same width.

2. The plastic container device of claim 1, wherein when the lid is rotatably screwed on to the outside of the container, the two separate seals prevent any leakage of the liquid sample from the interior of the container and any air seepage into or out of the interior of the container.

3. The plastic container device of claim 1, wherein the volume capacity of the contents of the container ranges from 500 ml down to 40 ml.

4. The plastic container device of claim 1, wherein the lid gasket and the container gasket have the same diameter.

5. The plastic container device of claim 1, wherein the container gasket has a smaller diameter than the lid gasket.

* * * * *